(12) United States Patent
Miyata

(10) Patent No.: US 6,497,830 B2
(45) Date of Patent: Dec. 24, 2002

(54) ULTRAVIOLET LIGHT ABSORBER AND ITS USE

(75) Inventor: Shigeo Miyata, Fukuoka-ken (JP)

(73) Assignee: Kabushiki Kaisha Kaisui Kagaku Kenkyujo, Fukuoka-ken (JP)

(*) Notice: Subject to any disclaimer, the term of this patent is extended or adjusted under 35 U.S.C. 154(b) by 0 days.

(21) Appl. No.: 09/805,151

(22) Filed: Mar. 14, 2001

(65) Prior Publication Data

US 2001/0051137 A1 Dec. 13, 2001

(30) Foreign Application Priority Data

Mar. 14, 2000 (JP) .......................... 2000-069796
Feb. 2, 2001 (JP) .......................... 2001-026802

(51) Int. Cl.$^7$ .............................. F21V 9/04; A61K 7/42; C08K 3/10
(52) U.S. Cl. ................. 252/588; 252/584; 423/263; 423/594; 423/598; 423/600; 423/622; 424/59; 524/435; 524/413
(58) Field of Search ................. 252/584, 588; 423/263, 594, 598, 600, 622; 424/59; 523/135; 524/413, 435

(56) References Cited

U.S. PATENT DOCUMENTS 3,538,022 A * 11/1970 Bowman .................... 423/600
5,424,055 A    6/1995 Hayashi et al.
5,611,852 A *  3/1997 Pfaff et al. .................. 423/622
5,750,609 A *  5/1998 Nosu .......................... 423/594

FOREIGN PATENT DOCUMENTS

EP         0 737 711         10/1996

* cited by examiner

Primary Examiner—Philip Tucker
(74) Attorney, Agent, or Firm—Wenderoth, Lind & Ponack, L.L.P.

(57) ABSTRACT

An ultraviolet light absorber containing, as an active ingredient, a zinc oxide type solid solution which is represented by the formula (1), $$(Zn)_{1-x}M^{3+}{}_{x-\delta}O \qquad (1)$$

wherein $M^{3+}$ is a trivalent metal such as Al, Fe, Ce or Ti, x is a number in the range of $0<x<=0.2$, and $\delta$ is a cationic lattice defect, and has an average secondary particle diameter of from 0.1 to 1.5 μm in a plate form and a BET specific surface area of at least 5 m$^2$/g, an ultraviolet light resistant resin composition containing a resin and the above zinc oxide type solid solution and a sun block cosmetic material containing the above zinc oxide type solid solution.

12 Claims, 3 Drawing Sheets

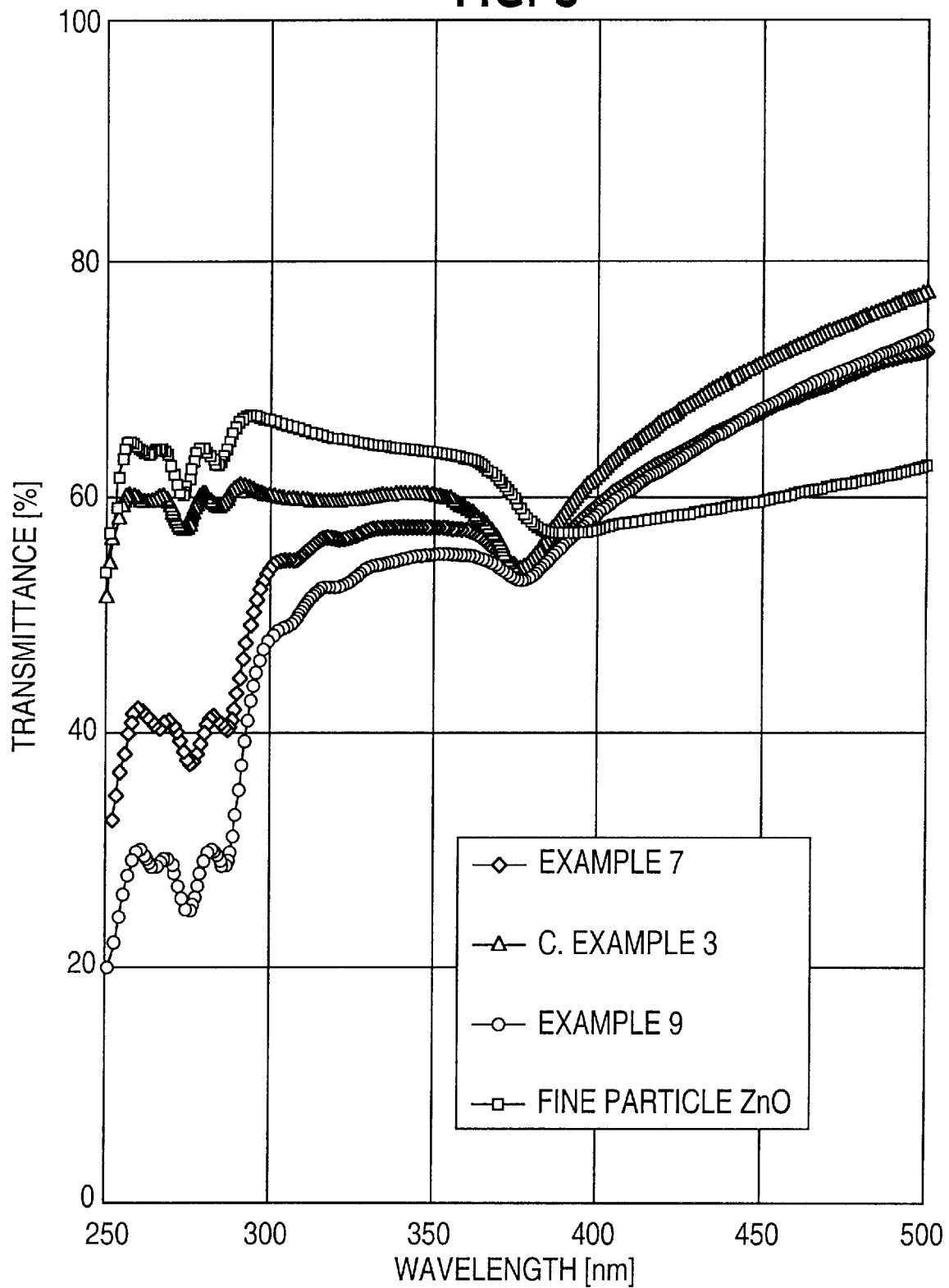

ULTRAVIOLET LIGHT ABSORBER AND ITS USE

FIELD OF THE INVENTION

The present invention relates to a novel ultraviolet light absorber, an ultraviolet light resistant resin composition containing the above ultraviolet light absorber and a sun block cosmetic material containing the above ultraviolet light absorber.

PRIOR ART OF THE INVENTION

Organic high molecular weight compounds (to be sometimes referred to as "resin" hereinafter) such as plastics, lubbers and fibers are used in large quantity. When these organic high molecular weight compounds are exposed to a light, they are deteriorated in physical properties by ultraviolet light. Therefore, an ultraviolet light absorber is incorporated therein to impart ultraviolet light resistance. Further, a human skin also undergoes sunburn, pigmentation or cytoclasis by ultraviolet light, which induces light-irritable dermatitis or malignancy. Further, the occurrence of geroderma is also advanced. As a preventer for the above problems, a sun block cosmetic material containing an ultraviolet light absorber is commercially available.

The ultraviolet light absorber includes an organic compound-containing ultraviolet light absorber such as a benzotriazole-containing ultraviolet light absorber or a benzophenone-containing ultraviolet light absorber, and an inorganic compound-containing ultraviolet light absorber such as titanium oxide or zinc oxide. The organic compound-containing ultraviolet light absorber is excellent in transparency and also excellent in ultraviolet light absorption. The above type ultraviolet light absorber is therefore used as an ultraviolet light absorber in most cases and the usage thereof is large. In contrast, the inorganic compound-containing ultraviolet light absorber is poor in transparency and it is inferior to the organic compound-containing ultraviolet light absorber in terms of ultraviolet light absorption. The inorganic compound-containing ultraviolet light absorber has been unusually used as an ultraviolet light absorber. However, the inorganic compound-containing ultraviolet light absorber has high safety and it has attracted attention in recent years. Therefore, zinc oxide or titanium oxide having ultrafine particles is developed and transparency or ultraviolet light absorption is improved. As a result, the above zinc oxide or titanium oxide has come to be used mainly in a sun block cosmetic material in place of the organic compound-containing ultraviolet light absorber. Furthermore, recently, a zinc oxide type solid solution has been proposed as a novel ultraviolet light absorber.

In recent years, the standard of living and the average life expectancy are increased so that requirements for the safety of a product have been more and more increased. In other words, the term "safety" refers to non-toxicity or low toxicity and no correspondence to environmental hormones. The safety of the ultraviolet light absorber is also required. It is pointed out that the above-described organic compound-containing ultraviolet light absorber has problems concerning toxicity or environmental hormones. On the other hand, the inorganic compound-containing ultraviolet light absorber is poor in transparency and has a problem of dispersibility in a resin while it is safe. Therefore, it is difficult to use the inorganic compound-containing ultraviolet light absorber in a resin.

A solar spectrum can be divided into the ultraviolet region (290–400 nm), the visible region (400–760 nm) and the near-infrared region (>760 nm). The ultraviolet region can be further divided into the UVA region, the UVB region and the UVC region. The UVB region is 290–320 nm and the UVB region is a region where the largest effect with regard to the sunburn of a skin is produced. The UVC region is 200–290. The ozone layer absorbs an ultraviolet light in the UVC region and no ultraviolet light in the UVC region reaches the earth's surface. The UVA region is 320–400 nm. While the UVA region causes sunburn, its sunburn power is smaller than that of the UVB region. For example, the erythema causability of the UVA region is small so that no acute inflammation is caused. Conventionally, there has been therefore used a sun block agent intercepting an ultraviolet light in the UVB region. The use of such a sun block agent delays the occurrence of sunburn recognizable by visual observation, which results in exposure to the sunlight for a long time in many cases. Recently, it is come to be known that an ultraviolet light in the UVA region penetrates a skin and impairs the skin. That is, it is said that an ultraviolet light in the UVA region is the main cause of 30 to 40% of skin cancer. Further, it is also said that an ultraviolet light in the UVA region accelerates skin cancer by inhibiting an enzyme which cures cells impaired by a UVB radiation. Furthermore, it is also reported that an ultraviolet light in the UVA region penetrates a skin deeper than an ultraviolet light in the UVB region, causes a change in a blood vessel, causes an early aging of a skin and adds an additional deleterious effect to the deleterious effect of an ultraviolet light in the UVB region.

In recent years, there are developed fine particles of zinc oxide and titanium oxide and these fine particles of zinc oxide and titanium oxide are used in a sun block cosmetic material. However, the formation of fine particles intensifies cohesion and deteriorates dispersibility and in addition it causes poor extension and deteriorates usability. Further, light resistance is deteriorated by a photocatalyst activity. The formation of fine particles involves these new problems. Further, titanium oxide having ultrafine particles is still poor in transparency and additionally poor in the absorption in the UVA region. Zinc oxide having ultrafine particles has good transparency but it has a problem that the absorption in the UVB region is poor.

JP-A-8-337768 discloses a zinc oxide type solid solution which is represented by the formula (2),

$$(Zn_y M^{2+}z)_{1-x} M^{3+}_x O_{1+x/2} \qquad (2)$$

wherein $M^{2+}$ is at least one metal selected from the group consisting of Mg, Ca, Ni and Cu, $M^{3+}$ is Al and/or Fe, and each of x, y and z respectively satisfies $0.2<x\leq0.4$, $(y+z)=1$, and $0\leq z<=0.75$,
and which has an aspect ratio of from 2 to 200 and an average secondary particle diameter of 5 μm.

This solid solution has good transparency but it has poor absorption of an ultraviolet light, in particular an ultraviolet light in the UVA region.

SUMMARY OF THE INVENTION

It is an object of the present invention to provide an ultraviolet light absorber containing a zinc oxide type solid solution which ultraviolet light absorber absorbs ultraviolet lights in both the UVA region and the UVB region well, and is excellent in hydration resistance and an ultraviolet light resistant resin composition containing the above ultraviolet light absorber.

It is another object of the present invention to provide an ultraviolet light resistant resin composition suitable for providing a resin-containing packaging material for food or the like which packaging material can prevent deterioration of food or the like by ultraviolet light.

According to the present invention, there is provided an ultraviolet light absorber containing, as an active ingredient, a zinc oxide type solid solution which is represented by the formula (1), $$(Zn)_{1-x}M^{3+}_{x-\delta}O \quad (1)$$

wherein $M^{3+}$ is a trivalent metal such as Al, Fe, Ce or Ti, x is a number in the range of $0 < x \leq 0.2$, preferably $0.05 < x < 0.2$, particularly preferably $0.06 \leq x \leq 0.18$, and $\delta$ is a cationic lattice defect, and has an average secondary particle diameter of from 0.1 to 1.5 μm, preferably 0.4 to 1.0 μm, in a plate form and a BET specific surface area of from 5 to less than 20 m²/g or a BET specific surface area of at least 20 m²/g.

According to the present invention, there is further provided an ultraviolet light absorber according to the above, wherein the surface of the solid solution of the formula (1) is coated with at least one oxide selected from oxides of Fe, Ce and Ti.

According to the present invention, there is further provided an ultraviolet light resistant resin composition containing 100 parts by weight of a resin and 0.01 to 10 parts by weight of the zinc oxide type solid solution which is represented by the formula (1) and has an average secondary particle diameter of from 0.1 to 1.5 μm, preferably from 0.4 to 1.0 μm, in a plate form and a BET specific surface area of from 5 to less than 20 m²/g or a BET specific surface area of at least 20 m²/g.

According to the present invention, there is further provided a sun block cosmetic material containing, as an active ingredient, the above zinc oxide type solid solution which is represented by the formula (1) and has an average secondary particle diameter of from 0.1 to 1.5 μm, preferably from 0.4 to 1.0 μm, in a plate form and a BET specific surface area of from 5 to less than 20 m²/g or a BET specific surface area of at least 20 m²/g.

BRIEF DESCRIPTION OF DRAWINGS

FIG. 3 shows a graph showing the transmittance measurement results of Examples 7 and 9 and Comparative Example 3.

DETAILED DESCRIPTION OF THE INVENTION

Figure 1:
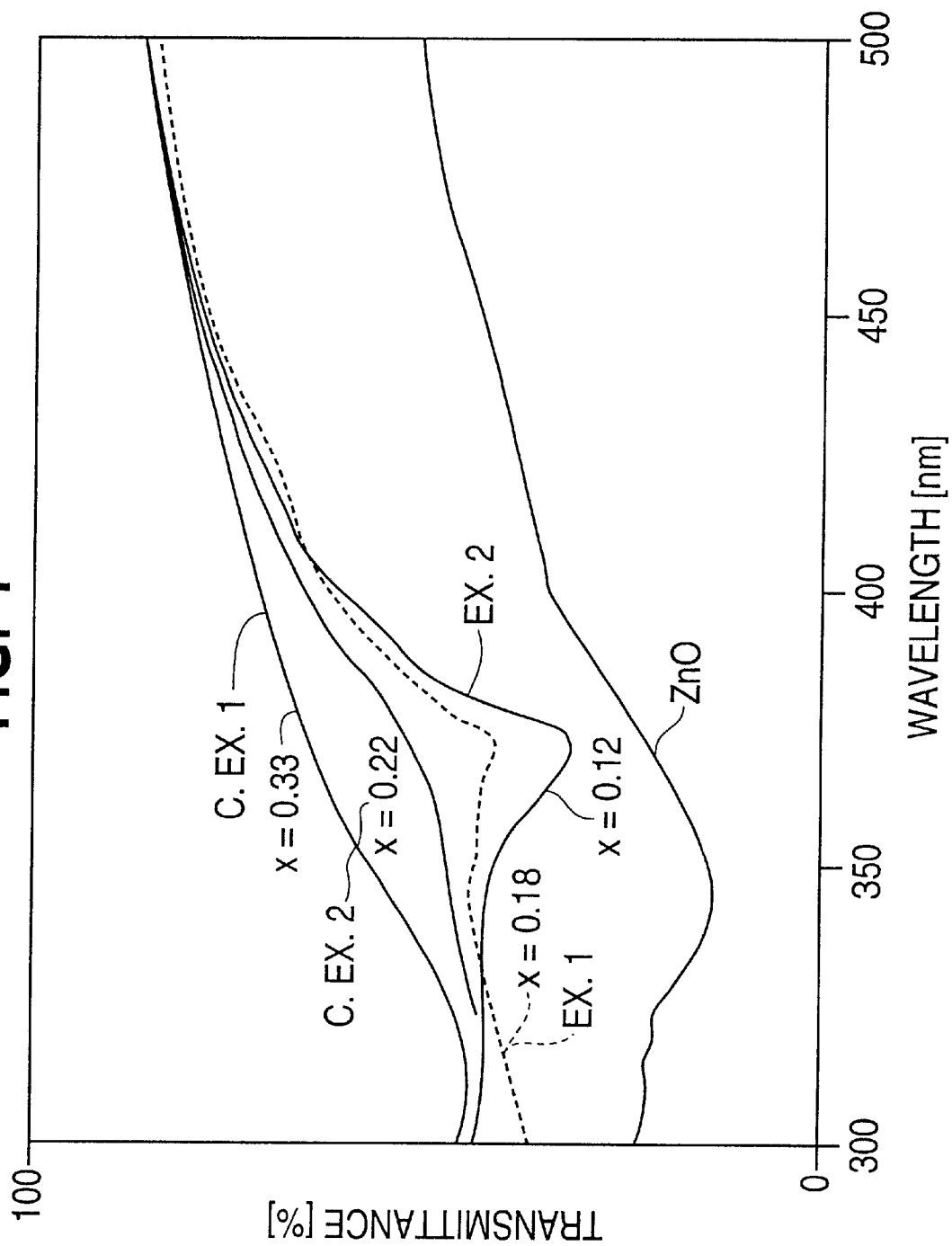
FIG. 1 shows a graph showing the transmittance measurement results of Examples 1 and 2 and Comparative Examples 1 and 2.

The present inventors have made diligent studies for providing an ultraviolet light absorber which absorbs an ultraviolet light in both the UVA region and the UVB region and an ultraviolet light resistant resin composition containing the above ultraviolet light absorber and as a result have found that the solid solution of the formula (1) in which x is in the range of $0 < x \leq 0.2$ and which has a BET specific surface area in the specific range is especially practicable. There are differences between properties shown when the BET specific surface area is from 5 to less than 20 m²/g and properties shown when the BET specific surface area is 20 m²/g or more. The solid solution of the formula (1) which solid solution has a BET specific surface area of from 5 to less than 20 m²/g, preferably from 10 to less than 20 m²/g, is excellent in hydration resistance but slightly poor in transparency.

The zinc oxide type solid solution of the formula (1) is a solid solution compound in which a trivalent metal such as Al is substitutionally dissolved in ZnO and its secondary particles have a plate form. The crystal structure thereof is the same as the crystal structure of zinc oxide. It is no matter that a small amount of divalent metal other than zinc may be dissolved therein. Aluminum and/or iron are most preferred as a trivalent metal. The range of x is $0 < x \leq 0.2$, preferably $0.05 < x < 0.2$, particularly preferably $0.06 \leq x \leq 0.18$.

For improving the transparency of a resin when incorporated into the resin or for improving the transparency when used as a cosmetic article, it is required that the zinc oxide type solid solution of the formula (1) has a small primary particle diameter, i.e., a large BET specific surface area and a moderately small secondary particle diameter.

For satisfying the above requirements, it is needed to use a zinc oxide type solid solution of the formula (1) which solid solution has a BET specific surface area of at least 20 m²/g, preferably at least 40 m²/g, more preferably at least 60 m²/g, and an average secondary particle diameter of from 0.1 to 1.5 μm, preferably 0.2 to 1.0 μm, more preferably 0.3 to 0.7 μm, in a plate form.

When the average secondary particle diameter is smaller than 0.1 μm, dispersibility is poor.

When the BET specific surface area is in the range of from 5 to less than 20 m²/g, preferably in the range of from 10 to less than 20 m²/g, transparency is slightly poor but hydration resistance and absorption of an ultraviolet light are excellent. When the average secondary particle diameter is in the above range, regardless of the BET specific surface area, a resin composition containing the above zinc oxide type solid solution in a resin has excellent dispersibility or a cosmetic article containing the above zinc oxide type solid solution has excellent extension and adhesion.

For attaining a purpose such as improving the ultraviolet light absorption capability of the ultraviolet light absorber of the present invention or, when used for a cosmetic article, approximating the color of the cosmetic article to a fresh color, it is recommended that the surface of the solid solution of the present invention is coated with at least one oxide selected from oxides of Ti, Fe and Ce. The amount of the oxide to be used for covering is approximately 0.1 to approximately 50% by weight, preferably 1 to 25% by weight, based on the weight of the solid solution.

The ultraviolet light absorber of the present invention is preferably surface-treated with an oleophilic surface-treating agent for improving the compatibility and dispersibility of the ultraviolet light absorber with/in a resin or improving the water repellency of a cosmetic article containing the ultraviolet light absorber of the present invention. Preferable surface-treating agents will be shown below. The preferable surface-treating agents include higher fatty acids such as stearic acid, lauric acid and behenic acid; alkali metal salts of the above higher fatty acids (anionic surfactant); phosphates such as stearyl acid phosphate, lauryl acid phosphate and oleyl acid phosphate; alkali metal salts or ethanol amine salts of the above phosphates; fluorine-containing coating agents such as polyfuloroalkyl phosphate diethanol amine salt and poly(perfluoroalkylethyl acrylate); coupling agents such as vinylethoxysilane, gamma-methacryloxypropyltrimethoxysilane, an isopropyl triisostearoyle titanate-containing coupling agent and an aluminum-containing coupling agent and esters of a polyvalent alcohol and a fatty acid such as glycerine monostearate.

The solid solution of the formula (1) may be surface treated with a surface-treating agent by a known wet method or a known dry process. In the wet method, for example, a liquid-state or emulsion-state surface-treating agent dissolved in alcohol or in a mixed solvent of alcohol and water is added to a mixture prepared by dispersing the solid solution in a solvent such as methanol, ethanol or water, and it is sufficient to fully mix the resultant mixture under heat or without heating. The amount of a surface-treating agent can be selected as required, while the amount of a surface-treating agent is preferably approximately 0.1 to 10% by weight based on the weight of the solid solution. After the surface treatment, treatments such as filtration, drying, pulverization and classification may be properly selected and carried out as required, to obtain a final product.

The ultraviolet light absorber of the present invention is produced by hydrothermally treating a hydrotalcite represented by the formula (3),

$$(Zn)_{1-x}M^{3+}(OH)_2A^{n-}_{x/n}mH_2O \qquad (3)$$

wherein $M^{3+}$ is a trivalent metal such as Al, Fe, Ce or Ti, preferably Al and/or Fe, $A^{n-}$ is anion having a valence of n (n is 1 to 6) such as $Cl^-$ or $CO_2^{2-}$, x is a number in the range of $0 \leq x \leq 0.2$, and m is a number of in the range of $0 \leq m \leq 2$, or a mixture of the hydrotalcite and zinc oxide at approximately 100 to 170° C., preferably approximately 110 to 150° C., for at least 1 hour, preferably for 10 to 20 hours, then, filtrating it, drying it and calcining it at approximately 300 to 800° C., preferably approximately 400 to 700° C.

When the solid solution having a BET specific surface area of less than 20 m²/g, provided by the present invention, is prepared, the calcining temperature is set at approximately 600 to 1,100° C., preferably approximately 700 to 1,000° C., particularly preferably 700 to 900° C. The size of the BET specific surface area is controlled mainly by the calcining temperature, while it must be properly changed depending upon the properties and kind of hydrotalcite to be used.

The hydrotalcite of the formula (3) can be produced by a known method. For example, a mixed aqueous solution of a water-soluble zinc salt such as zinc chloride, zinc nitrate or zinc sulfate and a water-soluble trivalent metal salt such as aluminum chloride, aluminum nitrate, aluminum sulfate, ferric chloride or cerium chloride is mixed and reacted with stirring while the pH of the mixed solution is maintained at approximately 6 or higher, preferably approximately 7 or higher with an alkali such as sodium hydroxide, sodium carbonate or potassium hydroxide.

The production method comprising coating the solid solution of the formula (1) with at least one oxide selected from Ti, Fe and Ce is as follows. The hydrotalcite of the formula (3) is dispersed in water, at least one water-soluble salt of Ti, Fe and Ce is added thereto with stirring to perform hydrolyzation, then, a filtration, washing with water and drying are carried out and then, the resultant substance is calcined at approximately 300 to 800° C. or, when the BET specific surface area is less than 20 m²/g, at approximately 600 to 1,100° C. Otherwise, the solid solution of the formula (1) is dispersed in water or alcohol containing a small amount of water, a water-soluble or alcohol-dissoluble compound of Ti, Fe or Ce is added with stirring, to perform hydrolyzation, a solid-liquid separation is carried out, and the solid is calcined at approximately 300 to 800° C. In the above coating conditions, an alkali such as sodium hydroxide, ammonium or sodium acetate may be added before or after the hydrolyzation to neutralize part of the metal or all the metal. Further, the water-soluble salt of Ti, Fe or Ce may be replaced with a sol thereof.

The amount of the metal oxide used for coating is 0.5 or less, preferably 0.01 to 0.2, in the atom weight ratio based on zinc of 1, and the amount of the metal is 50% by weight or less, preferably 1 to 25% by weight, based on the zinc oxide type solid solution.

The resin used in the present invention includes for example thermoplastic resins such as polyethylene, polypropylene, polystyrene, ABS, polyacrylate, polycarbonate, polyethylene terephthalate, polymethacrylate, polyamide, polyester, an ethylene vinyl acetate copolymer, polymethylpentene, polybutene, polyvinyl chloride and polyvinyl acetate; thermosetting resins such as a phenol resin, a melamine resin, an epoxy resin, an unsaturated polyester resin and an alkyd resin; rubbers such as EPDM, SBR, NBR, butyl rubber, isoprene rubber and chlorosulfonated polyethylene rubber; and synthetic fibers such as an acrylic fiber, an acetate fiber, nylon, a polyester fiber, a polypropylene fiber and a polyethylene fiber. However, the resin is not limited to these.

The method of mixing and kneading the resin and the ultraviolet light absorber of the present invention is not specially limited. Any mixing means may be adopted, so long as the means can uniformly mix both the components. For example, there may be used an extruder, a roll, a Banbury mixer or a homogenizer. No special limitation is also imposed upon the molding method. For example, it includes an injection molding, an extrusion molding, a blow molding, a press molding, a rotation molding, a calender molding, a sheet forming molding, a vacuum molding and spinning.

The transparent ultraviolet light resistant resin composition of the present invention may contain a variety of additives as required. Examples of the additives include an anti-oxidant, a lubricant, an antistatic agent, a pigment, a forming agent, a plasticizer, a filler, a reinforcing agent, a crosslinker, a mildewproofing agent and an anti-adhesion agent.

Effect of the Invention

According to the present invention, there are provided a nontoxic inorganic ultraviolet light absorber which is excellent in both transparency (high visible light transmittance) and ultraviolet light absorption, and excellent in dispersibility and extension, an ultraviolet light resistant resin composition containing the above absorber and a sun block cosmetic material containing the above absorber. Further, there are provided an ultraviolet light absorber having the above properties and additionally excellent hydration resistance, an ultraviolet light resistant resin composition containing the above absorber and a sun block cosmetic material containing the above absorber.

The present invention will be explained more in detail with reference to Examples hereinafter.

EXAMPLE 1

An aluminum nitrate/zinc nitrate mixed aqueous solution ($Al^{3+}$=0.27 mol/l, $Zn^{2+}$=1.23 mol/l) and a sodium hydroxide aqueous solution (4 mol/l) were added to an over flow type reaction tank having a capacity of 3 liters and containing 2 liters of water in an adding rate of 100 ml/min. and about 75 ml/min. respectively with stirring. The reaction pH was kept at about 7 by controlling the supply of an sodium hydroxide aqueous solution and the mixture was allowed to react at a temperature of about 30° C. The resultant reaction mixture containing a white precipitate in the form of a slurry was filtered under reduced pressure, washed thoroughly with a sodium carbonate aqueous solution and emulsified. The resultant emulsified product was placed in an autoclave and hydrothermally treated at 120° C. for 20 hours. The hydrothermally treated product was filtered, washed with water and dried.

The crystal structure of the dried product was identified by X-ray diffraction pattern, and it was confirmed that the dried product was hydrotalcites. The dried product was pulverized and calcined at 500° C. for 1 hour. The X-ray diffraction pattern of the calcined powder was measured, and the pattern showed only the diffraction pattern of ZnO, however, the X-ray diffraction pattern thereof shifted toward a little higher angle side. It was therefore found to be a solid solution of Al in ZnO. It had a BET specific surface area of 59 m$^2$/g. The powder was treated in isopropyl alcohol with an ultrasonic for about five minutes to be dispersed therein, then the particle size distribution of secondary particles was measured with a particle size distribution measuring device according to a laser diffraction method. As a result thereof, the average secondary particle diameter was 0.78 μm and the maximum secondary particle diameter was 2.3 μm. The calcined powder had the following chemical composition.

$Zn_{0.µ}Al_{0.18-\delta}O$ 100 g of the powder was added to 500 ml of ethyl alcohol, and 2 g of lauric acid, which was dissolved in 50 ml of ethylalcohol under heat, was added to carry out a surface-treatment under stirring with a homogenizer at 10,000 r.p.m for about 10 minutes, and the resultant mixture was filtered, dried and pulverized to obtain a powder. FIG. 1 shows the results of measured light transmittance of the pulverized powder.

EXAMPLE 2

A dried powder was prepared in the same manner as in Example 1 except that the aluminum nitrate/zinc nitrate mixed aqueous solution was replaced with an aluminum nitrate/zinc nitrate mixed aqueous solution ($Al^{3+}$=0.18 mol/l, $Zn^{2+}$=1.32 mol/l). The dried product showed X-ray diffraction pattern of hydrotalcite and a little amount of ZnO. The dried product was pulverized and calcined at 500° C. for 1 hour. The calcined powder showed an X-ray diffraction pattern which slightly shifted to a high angle side, while it was a diffraction pattern of ZnO alone. It was therefore found to be a solid solution of Al in ZnO. The calcined powder had a BET specific surface area of 52 m$^2$/g, an average secondary particle diameter of 0.66 μm and the maximum secondary particle diameter of 1.81 μm. The calcined powder had the following chemical composition.

$Zn_{0.o}Al_{0.12-\delta}O$

FIG. 1 shows the results of measured light transmittance of the calcined powder.

EXAMPLE 3

A dried product was prepared in the same manner as in Example 1 except that the aluminum nitrate/zinc nitrate mixed aqueous solution was replaced with an aluminum nitrate/zinc nitrate mixed aqueous solution ($Al^{3+}$=0.09 mol/l, $Zn^{2+}$=1.41 mol/l). The dried product showed X-ray diffraction pattern of hydrotalcite and ZnO. The dried powder was pulverized and calcined at 400° C. for 1 hour. The calcined powder showed an X-ray diffraction pattern which slightly shifted to a high angle side, while it was a diffraction pattern of ZnO alone. It was therefore found to be a solid solution of Al in ZnO. The calcined powder had a BET specific surface area of 38 m$^2$/g, an average secondary particle diameter of 0.94 μm and the maximum secondary diameter of 2.6 μm. The pulverized powder had the following chemical composition.

$Zn_{0.94}Al_{0.06-67}O$

Figure 2:
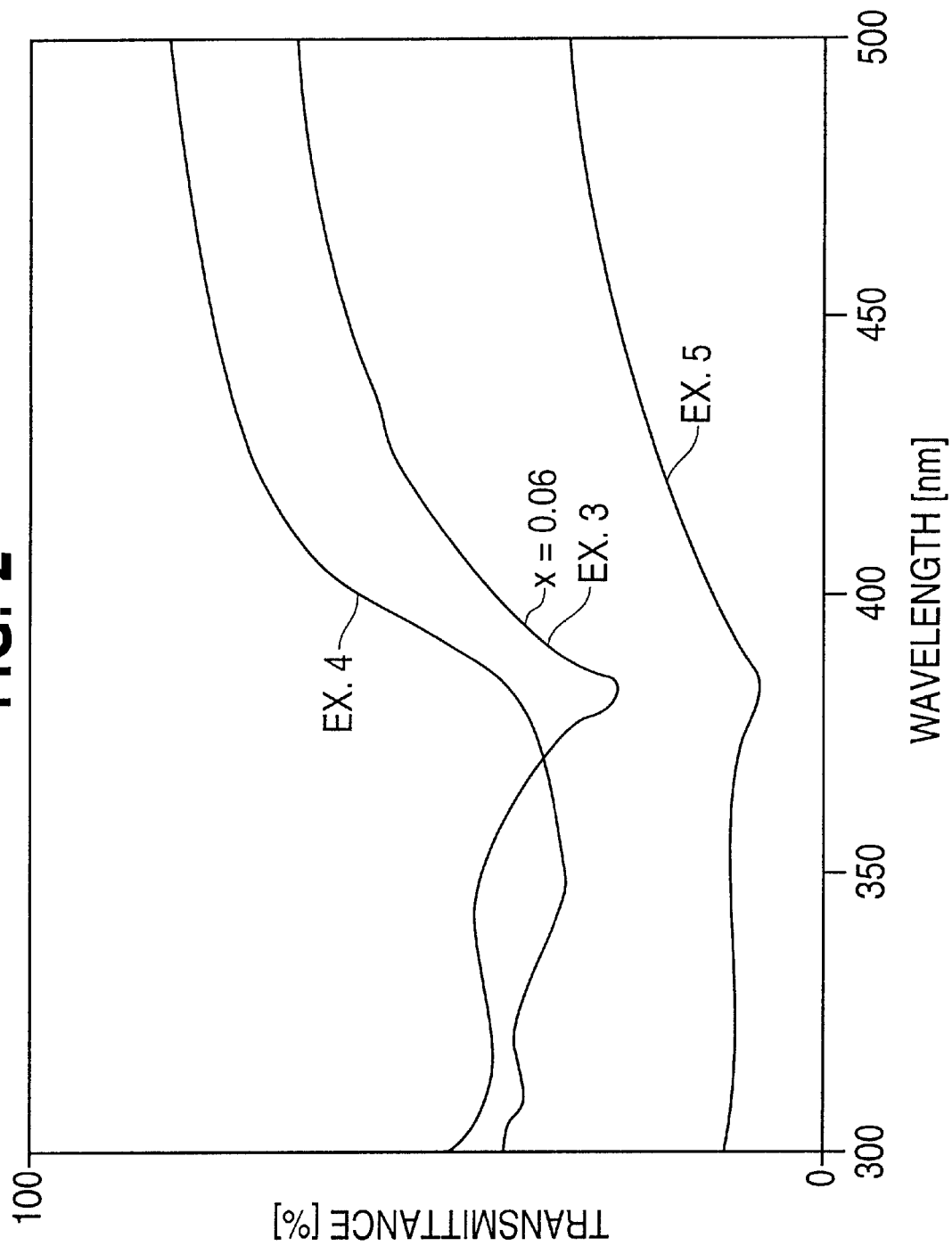
FIG. 2 shows a graph showing the transmittance measurement results of Examples 3, 4 and 5.

FIG. 2 shows the results of measured light transmittance of the calcined powder.

EXAMPLE 4

50 g of the dried product obtained in Example 2, which was not calcined and showed the diffraction pattern of hydrotalcite and a small amount of ZnO, was added to 500 ml of deionized water and dispersed therein with a homogenizer, and then 200 ml of deionized water dissolving 10 g of cerium chloride ($CeCl_3 \cdot 7H_2O$) was added under stirring with a homogenizer. Then, 0.2 mol/liter of NaOH aqueous solution was added to control a pH about 8. The resultant product was filtered, washed with water, dried and pulverized. The pulverized powder was calcined at 400° C. for 1 hour. The calcined powder showed an X-ray diffraction pattern which slightly shifted to a high angle side, while it was a diffraction pattern of ZnO, and a weak X-ray diffraction pattern of $CeO_2$. The calcined powder had a BET specific surface area of 56 m$^2$/g, an average secondary particle diameter of 0.56 μm and the maximum secondary diameter of 1.81 μm. The calcined powder had the following chemical composition.

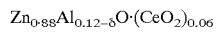

$Zn_{0.88}Al_{0.12-\delta}O \cdot (CeO_2)_{0.06}$

FIG. 2 shows the results of measured light transmittance of the calcined powder.

EXAMPLE 5

A dried product was prepared in the same manner as in Example 1 except that the aluminum nitrate/zinc nitrate mixed aqueous solution was replaced with an aluminum nitrate/zinc nitrate mixed aqueous solution ($Al^{3+}$=0.09 mol/l, $Zn^{2+}$=0.91 mol/l) and that the reaction pH was kept at about 11. The obtained dried product showed X-ray diffraction pattern of hydrotalcite and a little amount of ZnO. About 2 liters of water was added to 100 g of the dried product and dispersed with a homogenizer. 100 ml of an aqueous solution containing 10 g of $FeCl_2 \cdot 4H_2O$ was added to the dispersion with stirring and stirred for 30 minutes with a homogenizer. The dispersion was filtered, washed with water, dried and pulverized, and calcined at 400° C. for 1 hour. The calcined powder showed a color near to flesh-color, and showed an X-ray diffraction pattern which slightly shifted to a high angle side, while it was a diffraction pattern of ZnO alone. It was therefore found to be a solid solution of Al and Fe in ZnO. The calcined powder had a BET specific surface area of 39 m$^2$/g, an average secondary particle diameter of 0.72 μm and the maximum secondary particle diameter of 1.8 μm. The calcined powder had the following chemical composition.

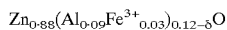

FIG. 2 shows the results of measured light transmittance of the calcined powder.

COMPARATIVE EXAMPLE 1

A dried product was prepared in the same manner as in Example 1 except that the aluminum nitrate/zinc nitrate mixed aqueous solution was replaced with an aluminum nitrate/zinc nitrate mixed aqueous solution ($Al^{3+}$=0.5 mol/l, $Zn^{2+}$=1.0 mol/l). The obtained dried product showed X-ray diffraction pattern of hydrotalcite. The dried product had the following chemical composition.

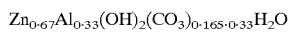

The dried product was pulverized and calcined at 600° C. for 1 hour. The calcined powder showed an X-ray diffraction pattern which slightly shifted to a high angle side, while it was a diffraction pattern of ZnO alone. It was therefore found to be a solid solution of Al in ZnO. The calcined powder had a BET specific surface area of 110 $m^2$/g, an average secondary particle diameter of 0.45 μm and the maximum secondary particle diameter of 1.6 μm. The calcined powder had the following chemical composition.

FIG. 1 shows the results of measured light transmittance of the calcined powder.

COMPARATIVE EXAMPLE 2

A dried product was prepared in the same manner as in Example 1 except that the aluminum nitrate/zinc nitrate mixed aqueous solution was replaced with an aluminum nitrate/zinc nitrate mixed aqueous solution ($Al^{3+}$=0.33 mol/l, $Zn^{2+}$=1.17 mol/l). The obtained dried product showed X-ray diffraction pattern of hydrotalcite.

The dried product was pulverized and calcined at 500° C. for 1 hour. The calcined powder showed an X-ray diffraction pattern which slightly shifted to a high angle side, while it was a diffraction pattern of ZnO alone. It was therefore found to be a solid solution of Al in ZnO. The calcined powder had a BET specific surface area of 78 $m^2$/g, an average secondary particle diameter of 0.87 μm and the maximum secondary particle diameter of 2.1 μm. The calcined powder had the following chemical composition.

FIG. 1 shows the results of measured light transmittance of the calcined powder.

[Measurement of UV Absorption Spectra]

Each of ZnO type solid solutions obtained in Examples 1, 2, 3, 4 and 5 and Comparative Examples 1 and 2 and zinc flowers #1 as an ultraviolet light absorber was respectively added to obtain the following composition.

| Vinyl chloride resin | 100 parts by weight |
| --- | --- |
| Dioctylphthalate | 50 parts by weight |
| Calcium stearate | 1 part by weight |
| Zinc stearate | 0.4 part by weight |
| Ultraviolet light absorber | 0.1 part by weight |

The composition was previously mixed homogeneously, and then kneaded by an open-roll at 170° C. for 3 minutes. The sheet kneaded with the open-roll was preheated at 165° C. for 5 minutes, and molded at the pressure of about 120 kg/$cm^2$ for 5 minutes with a pressing machine to obtain a sheet having a thickness of 1.0 mm. Transmittance in the wavelength of 300–500 nm of the sheet was measured with a spectrophotometer. Vinyl chloride sheet which did not contain a ZnO solid solution was used as a contrast example to the sample sheet. FIGS. 1 and 2 show the measured results.

The results show that when x of a solid solution $Zn_{1-x}Al_{x-\delta}O$ is in the range of 0.2 or less, more especially, 0.18–0.06, the solid solution has the maximum UV absorption at about 380 nm and is excellent in transparency. The maximum UV absorption of ZnO is 340 nm. To the contrary, the maximum UV absorption of the solid solution is in the more lengthy side of about 40 nm. It shows that the UV absorption in the region of UVA (320–400 nm) of the solid solution is better than that of ZnO. When x of the solid solution is more than 0.2, more especially, more than 0.22, the solid solution is low in the UV absorption in the UVA region. When x of the solid solution is 0.04 or less, the maximum UV absorption of the solid solution has a tendency to shift to a short wavelength side, and UV absorption in the region of UVB and transparence have a tendency to become low. It is found that the solid solution having x of 0.18–0.06 is most preferable as an ultraviolet light absorber. Particularly preferably, x is near 0.12.

EXAMPLE 6

100 g of ZnO type solid solution powder obtained in Example 2 was added to 1 liter of ethyl alcohol, and dispersed homogeneously with a homogenizer. 50 ml of ethyl alcohol dissolving 2 g of lauric acid was added to the dispersion under a high speed stirring to carry out the surface-treatment. The stirring was continued for 10 minutes. The resultant mixture was filtered, washed with water, dried and pulverized to obtain a powder. The powder floated on water and showed an excellent water-repellent property. The powder showed a good slippery when it was extended by fingers.

EXAMPLE 7

An aluminum nitrate/zinc nitrate mixed aqueous solution ($Al^{3+}$=0.25 mol/l, $Zn^{2+}$=1.25 mol/l) and a sodium hydroxide aqueous solution (4 mol/l) were added to an over flow type reaction tank having a capacity of 3 liters and containing 2 liters of water previously, in an adding rate of 100 ml/min. and about 75 ml/min. respectively with stirring. The reaction pH was kept at about 11 by controlling the supply of a sodium hydroxide aqueous solution and the mixture was allowed to react at a temperature of about 30° C. The resultant reaction mixture containing a white precipitate in the form of a slurry was filtered under reduced pressure, washed thoroughly with a sodium carbonate aqueous solution and emulsified. The resultant emulsified product was placed in an autoclave and hydrothermally treated at 120° C. for 20 hours. The hydrothermally treated product was filtered, washed with water and dried.

The crystal structure of the dried product was identified by X-ray diffraction pattern, and it was confirmed that the dried product was hydrotalcite. The dried product was pulverized and then calcined at 770° C. for 1 hour. The X-ray diffraction pattern of the calcined powder was measured, and the pattern showed only the diffraction pattern of ZnO, while the X-ray diffraction pattern thereof shifted toward a little higher angle side. It was found that the calcined powder was a solid solution of Al in ZnO. It had a BET specific surface area of 15 m²/g. The calcined powder was treated in isopropyl alcohol with an ultrasonic for about five minutes to be dispersed therein, then the particle size distribution of secondary particles was measured with a particle size distribution measuring device according to a laser diffraction method. As a result thereof, the average secondary particle diameter was 0.58 μm and the maximum secondary particle diameter was 1.81 μm. The calcined powder had the following chemical composition.

$Zn_{0.83}Al_{0.17-\delta}O$

FIG. 3 shocks the results of measured light transmittance of the calcined powder.

EXAMPLE 8

A dried powder was prepared in the same manner as in Example 7 except that the aluminum nitrate/zinc nitrate mixed aqueous solution was replaced with an aluminum nitrate/zinc nitrate mixed aqueous solution ($Al^{2+}$=0.14 mol/l, $Zn^{2+}$=1.36 mol/l). The dried product showed X-ray diffraction pattern of hydrotalcite and a little amount of ZnO. The dried product was pulverized and calcined at 800° C. for 1 hour. The calcined powder showed an X-ray diffraction pattern which slightly shifted to a high angle side, while it was a diffraction pattern of ZnO alone. The calcined powder was a solid solution of Al in Zno. It had a BET specific surface area of 9 m²/g, an average secondary particle diameter of 0.62 μm and the maximum secondary particle diameter of 1.81 μm. The calcined powder had the following chemical composition.

$Zn_{0.91}Al_{0.09-\delta}O$

EXAMPLE 9

100 g of the dried powder obtained in Example 8, which was not calcined, was added to 2000 ml of water and dispersed therein with a homogenizer, and then 21 g of ferric chloride aqueous solution containing 39% by weight of $FeCl_3$ was added under stirring with the homogenizer. The stirring was continued for 30 minutes. The resultant product was filtered, washed with water, dried and pulverized. The pulverized powder Was calcined at 800° C. for 1 hour. The calcined powder showed a color near to a flesh color and showed an X-ray diffraction pattern which slightly shifted to a high angle side, while it was a diffraction pattern of ZnO alone. It was therefore found to be a solid solution of Al and Fe in Zno or a mixture of a solid solution of Al in ZnO and an amorphous $Fe_2O_3$. The calcined powder had a BET specific surface area of 12 m²/g, an average secondary particle diameter of 0.56 μm and the maximum secondary particle diameter of 1.81 μm. The calcined powder had the following chemical composition.

$Zn_{0.84}(Al_{0.11}Fe^{3+}_{0.05})_{0.16-67}O$ or

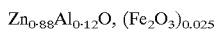

$Zn_{0.88}Al_{0.12}O$, $(Fe_2O_3)_{0.025}$

COMPARATIVE EXAMPLE 3

Hydrotalcite obtained in Example 7 was calcined at 600° C. for 1 hour. The calcined powder showed an X-ray diffraction pattern of ZnO alone. The calcined powder had a BET specific surface area of 56 m²/g, an average secondary particle diameter of 0.04 μm and the maximum secondary particle diameter of 1.81 μm. The chemical composition of the powder shows the same chemical composition as that of Example 7.

[Hydration Test]

5 g of a sample powder was added to Elren-meyer flask having a capacity of 300 ml and containing 100 ml of deionized water, and the mixture was stirred thoroughly. The mixture was placed in an oven at 50° C. for 24 hours to carry out hydration. The mixture was filtered under reduced pressure, washed with ethyl alcohol, placed in an oven at 30° C. for 30 minutes and dried. The X-ray diffraction pattern was measured at the condition of 40 KV and 20 mA. The extent of manufacture of hydrotalcite which shows the maximum peak at about d=7.6 Å were compared with the diffraction strength of the maximum peak.

TABLE 1

|  | Calcination temperature (° C.) | BET specific surface area (m²/g) | Peak strength [relative value] |
|---|---|---|---|
| Ex. 7 | 770 | 15 | 200 |
| Ex. 8 | 800 | 9 | 50 |
| Ex. 9 | 800 | 12 | 150 |
| C. Ex. 3 | 600 | 56 | 3600 |

Ex. = Example, C. Ex = Comparative Example

It is clear from the above results that ZnO type solid solution having a BET specific surface area of less than of 20 m²/g shows excellent resistance to hydration.

[Measurement of UV Absorption Spectrum]

Light transmittance in the wavelength range of 250–500 nm of ZnO type solid solution obtained in Example 7, 8 and 9, Comparative Example 3 and commercial available zinc flower having a BET specific surface area of 10 m²/g, an average secondary particle diameter 0.17 μm and the maximum secondary diameter of 0.96 μm was measured. A sample for measuring the above properties was prepared as follows. Castor oil and each powder which is 0.5% by weight based on the castor oil were mixed respectively, and the mixture was brayed with a mortar to obtain a uniform dispersion. The dispersion was pinched with two quartz boards having a thickness of 2 mm each to obtain a sheet having a thickness of 40 μm. The thickness of the sheet was controlled by placing spacers having a thickness of 40 μm between two quartz boards. FIG. 3 shows the measured results.

Zno type solid solution obtained in examples 7 to 9 showed better UV absorption than that of zinc oxide having fine particles, and also showed excellent in transmittance of visible light in the wavelength of 500 nm and in transparency.

What is claimed is:

1. An ultraviolet light absorber containing, as an active ingredient, a zinc oxide type solid solution which is represented by the formula (1),

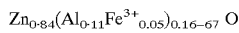

$$(Zn)_{1-x}M^{3+}{}_{x-\delta}O \qquad (1)$$

wherein $M^{3+}$ is at least one trivalent metal selected from the group consisting of Al, Fe, Ce or Ti, x is a number in the range of $0<x\leqq 0.2$, and $\delta$ is a cationic lattice defect, and has an average secondary particle diameter of from 0.1 to 1.5 μm in a plate form and a BET specific surface area of at least 5 m$^2$/g.

2. An ultraviolet light absorber according to claim 1, wherein the zinc oxide type solid solution has a BET specific surface area of from at least 5 m$^2$/g to less than 20 m$^2$/g.

3. An ultraviolet light absorber according to claim 1, wherein the zinc oxide type solid solution has a BET specific surface area of at least 20 m$^2$/g.

4. An ultraviolet light absorber according to claim 1, wherein $M^{3+}$ in the formula (1) is Al or Al and Fe.

5. An ultraviolet light absorber according to claim 1, wherein the surface of the solid solution of the formula (1) is coated with at least one oxide selected from oxides of Fe, Ce and Ti.

6. An ultraviolet light absorber according to claim 1, wherein the surface of the solid solution is surface treated with at least one oleophilic surface-treating agent selected from the group consisting of higher fatty acids, alkali metal salts of the higher fatty acids, phosphates, a fluorine-containing coating agent, silane-containing, titanate-containing and aluminum-containing coupling agents and an ester of a polyvalent alcohol and fatty acid.

7. An ultraviolet light resistant resin composition containing 100 parts by weight of a resin and 0.01 to 10 parts by weight of the zinc oxide type solid solution recited in claim 1, which is represented by the formula (1), $$(Zn)_{1-x}M^{3+}{}_{x-\delta}O \qquad (1)$$

wherein $M^{3+}$ is at least one trivalent metal selected from the group consisting of Al, Fe, Ce or Ti, x is a number in the range of $0<x\leqq 0.2$, and $\delta$ is a cationic lattice defect, and has an average secondary particle diameter of from 0.1 to 1.5 μm in a plate form and a BET specific surface area of at least 5 m$^2$/g.

8. An ultraviolet light resistant resin composition according to claim 7, wherein the zinc oxide type solid solution has a BET specific surface area of from at least 5 m$^2$/g to less than 20 m$^2$/g.

9. An ultraviolet light resistant resin composition according to claim 7, wherein the zinc oxide type solid solution has a BET specific surface area of at least 20 m$^2$/g.

10. An ultraviolet light resistant resin composition according to claim 7, wherein $M^{3+}$ in the formula (1) is Al or Al and Fe.

11. A sun block cosmetic material containing the zinc oxide type solid solution recited in claim 1 as an active ingredient.

12. An ultraviolet light absorber according to claim 2, wherein the surface of the solid solution is surface treated with at least one oleophilic surface-treating agent selected from the group consisting of higher fatty acids, alkali metal salts of the higher fatty acids, phosphates, a fluorine-containing coating agent, silane-containing, titanate-containing and aluminum-containing coupling agents and an ester of a polyvalent alcohol and fatty acid.

* * * * *